United States Patent
Hetherington et al.

(10) Patent No.: US 10,548,931 B1
(45) Date of Patent: *Feb. 4, 2020

(54) METHOD FOR TREATING CANNABIS INDUCED ANXIETY

(71) Applicant: CANOPY GROWTH CORPORATION, Smiths Falls (CA)

(72) Inventors: Mark Hetherington, Saskatoon (CA); Jason Green, Birch Hills (CA)

(73) Assignee: Canopy Growth Corporation, Smiths Falls, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/362,899

(22) Filed: Mar. 25, 2019

Related U.S. Application Data

(63) Continuation of application No. 15/996,034, filed on Jun. 1, 2018, now Pat. No. 10,279,000.

(60) Provisional application No. 62/514,621, filed on Jun. 2, 2017.

(51) Int. Cl.
| | | |
|---|---|---|
| *A61K 36/00* | (2006.01) |
| *A61K 36/185* | (2006.01) |
| *A61P 25/22* | (2006.01) |
| *A61K 47/22* | (2006.01) |
| *A61K 31/4453* | (2006.01) |
| *A61K 31/19* | (2006.01) |
| *A61K 45/06* | (2006.01) |
| *A61K 31/015* | (2006.01) |
| *A61K 31/05* | (2006.01) |
| *A61K 31/352* | (2006.01) |

(52) U.S. Cl.
CPC ............ *A61K 36/185* (2013.01); *A61K 47/22* (2013.01); *A61P 25/22* (2018.01); *A61K 31/015* (2013.01); *A61K 31/05* (2013.01); *A61K 31/19* (2013.01); *A61K 31/352* (2013.01); *A61K 31/4453* (2013.01); *A61K 45/06* (2013.01); *A61K 2300/00* (2013.01)

(58) Field of Classification Search
CPC .................................................... A61K 36/00
USPC ........................................................ 424/725
See application file for complete search history.

(56) References Cited

U.S. PATENT DOCUMENTS

2014/0245494 A1* 8/2014 Cohen ...................... A01H 5/12
800/298

* cited by examiner

*Primary Examiner* — Michael V Meller
(74) *Attorney, Agent, or Firm* — Stinson LLP

(57) ABSTRACT

Compositions and methods for the prevention and treatment of anxiety conditions associated with the use of *cannabis* are disclosed herein. The medicinal compositions include cannabidiol or cannabidiolic acid and one or more of the following compounds: bergamottin or dihydroxybergamottin, phloretin or a phloretin glycoside, piperine, apigenin or an apigenin glycoside and ursolic acid.

1 Claim, 3 Drawing Sheets

Bergamottin

Phloretin

Piperine

Ursolic Acid

Cannabidiol

Apigenin

Cannabidiolic Acid

Dihydroxybergamottin

Delta-9-THC

Delta-8-THC 11-hydroxy-delta-9-THC 11-nor-9-carboxy-delta-9-THC phlorizin apiin

METHOD FOR TREATING CANNABIS INDUCED ANXIETY

CROSS REFERENCE TO RELATED APPLICATIONS

This application is a continuation application of U.S. patent application Ser. No. 15/996,034, filed on Jun. 1, 2018, which claims priority to U.S. Provisional Application No. 62/514,621 filed on Jun. 2, 2017, each of which is hereby incorporated by reference in its entirety.

BACKGROUND OF THE DISCLOSURE

The following paragraphs are provided by way of background to the present disclosure. They are not however an admission that anything discussed therein is prior art or part of the knowledge of persons skilled in the art.

The present disclosure relates generally to compositions and methods for the prevention and treatment of anxiety conditions associated with the use of *cannabis*.

*Cannabis*, also commonly known as marijuana, is a preparation obtainable from the stems, leaves or dried flower buds of *Cannabis sativa* plants, and has long been used as a psychoactive medicinal drug, as well as for recreational purposes. In many jurisdictions, the use of medicinal *cannabis* by persons with a debilitating medical condition is permitted, and the use of *cannabis* as a medicament for the treatment of, for example, pain, nausea, AIDS-related weight loss and wasting, and multiple sclerosis is well known.

The primary psychoactive component of *cannabis* is a chemical compound known as tetrahydrocannabinol (THC), one of numerous related chemical compounds belonging to the cannabinoid class of compounds found in plants belonging to the genus *Cannabis*. Other cannabinoid compounds include, for example, cannabidiol (CBD), cannabinol (CBN) and tetrahydrocannabivarin (THCV). Some cannabinoids can be converted by the body, and once converted, mediate a psychoactive effect. Thus, for example, the cannabinoid $\Delta^9$-tetrahydrocannabinol can be metabolized to the derivative 11-hydroxy-$\Delta^9$-tetrahydrocannabinol, a more potent metabolite, which can readily cross the blood-brain barrier.

It is known that cannabinoid receptor proteins located in the brain mediate several important psychophysiological processes, including pain sensation, memory, mood and appetite. By interacting with cannabinoid receptor proteins, cannabinoid compounds modulate the function of cannabinoid receptors, as well as the psychophysiological processes that depend on these receptors.

One significant drawback associated with the use of *cannabis* is the commonly experienced side effect of a sensation of anxiety, which in certain instances, can be of such severity that hospitalization is necessary. *Cannabis*-induced anxiety has been reported regardless of the route of administration of the drug. Thus, inhalation, ingestion, sublingual, and buccal administration of *cannabis* all can lead to anxiolytic conditions. However, these conditions are typically most pronounced and least predictable when *cannabis* is ingested. This is generally attributable to the fact that the half-life of THC is substantially longer when *cannabis* is consumed orally than when THC is delivered via inhalation or other routes that bypass intestinal or hepatic degradation. Thus, peak blood plasma levels of THC are typically attained in 3-10 minutes from the time when *cannabis* is inhaled. By contrast, when *cannabis* is ingested, a maximum blood plasma THC concentration is typically reached in 1-2 hours. Typically, patients and individuals who are naïve to *cannabis* use and drug effects are at the most significant risk of the cascading effects of anxiety and can experience a lack of control of how long the anxiolytic condition will last. Thus, it will be clear from the foregoing that considerable drawbacks associated with the use of *cannabis* remain.

In view of the foregoing, there is a need in the art for method to ameliorate the anxiety effects associated with the use of *cannabis*.

BRIEF DESCRIPTION

The following paragraphs are intended to introduce the reader to the more detailed description that follows and not to define or limit the claimed subject matter of the present disclosure.

The present disclosure relates generally to compositions including *cannabis* and the use of these compositions in the prevention and treatment of anxiety conditions associated with the use of *cannabis*.

Accordingly, the present disclosure provides, in at least one embodiment, a medicinal composition for the prevention or treatment of an anxiolytic condition associated with the use of *cannabis*, the composition comprising cannabinol or cannabidiolic acid, and at least one of the following chemical compounds:
 (a) bergamottin or dihydroxybergamottin;
 (b) phloretin or a phloretin glycoside;
 (c) piperine;
 (d) apigenin or an apigenin glycoside; and
 (e) ursolic acid.

In another embodiment, the present disclosure provides a medicinal composition for the prevention or treatment of an anxiolytic condition associated with the use of *cannabis*, the composition comprising cannabidiol or cannabidiolic acid and at least two of the following chemical compounds:
 (a) bergamottin or dihydroxybergamottin;
 (b) phloretin or a phloretin glycoside;
 (c) piperine;
 (d) apigenin or an apigenin glycoside; and
 (e) ursolic acid.

In yet another embodiment, the present disclosure further provides, a medicinal composition for the prevention or treatment of an anxiolytic condition associated with the use of *cannabis*, the composition comprising cannabidiol or cannabidiolic acid and at least three of the following chemical compounds:
 (a) bergamottin or dihydroxybergamottin;
 (b) phloretin or a phloretin glycoside;
 (c) piperine;
 (d) apigenin or an apigenin glycoside; and
 (e) ursolic acid.

In yet another embodiment, the present disclosure further provides a medicinal composition for the prevention or treatment of an anxiolytic condition associated with the use of *cannabis*, the composition comprising cannabidiol or cannabidiolic acid and at least four of the following chemical compounds:
 (a) bergamottin or dihydroxybergamottin;
 (b) phloretin or a phloretin glycoside;
 (c) piperine;
 (d) apigenin or an apigenin glycoside; and
 (e) ursolic acid.

In yet another embodiment, the present disclosure further provides a medicinal composition for the prevention or treatment of an anxiolytic condition associated with the use of *cannabis*, the composition comprising the following chemical compounds:
- (a) bergamottin or dihydroxybergamottin;
- (b) phloretin or a phloretin glycoside;
- (c) piperine;
- (d) apigenin or an apigenin glycoside;
- (e) ursolic acid; and
- (f) cannabidiol or cannabidiolic acid.

In another embodiment, the present disclosure provides a method for preventing or treating an anxiolytic condition associated with the use of *cannabis*, the method comprising administering to a subject in need thereof, a medicinal composition comprising cannabidiol or cannabidiolic acid and at least one of the following chemical compounds:
- (a) bergamottin or dihydroxybergamottin;
- (b) phloretin or a phloretin glycoside;
- (c) piperine;
- (d) apigenin or an apigenin glycoside; and
- (e) ursolic acid, wherein the medicinal composition is administered prior to or following use of a *cannabis* product.

In another embodiment, the present disclosure provides a method for preventing or treating an anxiolytic condition associated with the use of *cannabis*, the method comprising administering to a subject in need thereof, a medicinal composition comprising cannabidiol or cannabidiolic acid and at least two of the following chemical compounds:
- (a) bergamottin or dihydroxybergamottin;
- (b) phloretin or a phloretin glycoside;
- (c) piperine;
- (d) apigenin or an apigenin glycoside; and
- (e) ursolic acid, wherein the medicinal composition is administered prior to or following use of a *cannabis* product.

In yet another embodiment, the present disclosure provides a method for preventing or treating an anxiolytic condition associated with the use of *cannabis*, the method comprising administering to a subject in need thereof, a medicinal composition comprising cannabidiol or cannabidiolic acid and at least three of the following chemical compounds:
- (a) bergamottin or dihydroxybergamottin;
- (b) phloretin or a phloretin glycoside;
- (c) piperine;
- (d) apigenin or an apigenin glycoside; and
- (e) ursolic acid, wherein the medicinal composition is administered prior to or following use of a *cannabis* product.

In another embodiment, the present disclosure provides a method for preventing or treating an anxiolytic condition associated with the use of *cannabis*, the method comprising administering to a subject in need thereof, a medicinal composition comprising cannabidiol or cannabidiolic acid and at least four of the following chemical compounds:
- (a) bergamottin or dihydroxybergamottin;
- (b) phloretin or a phloretin glycoside;
- (c) piperine;
- (d) apigenin or an apigenin glycoside; and
- (e) ursolic acid, wherein the medicinal composition is administered prior to or following use of a *cannabis* product.

In another embodiment, the present disclosure provides a method for preventing or treating an anxiolytic condition associated with the use of *cannabis*, the method comprising administering to a subject in need thereof, a medicinal composition comprising the following chemical compounds:
- (a) bergamottin or dihydroxybergamottin;
- (b) phloretin or a phloretin glycoside;
- (c) piperine;
- (d) apigenin or an apigenin glycoside;
- (e) ursolic acid; and
- (f) cannabidiol or cannabidiolic acid, wherein the medicinal composition is administered prior to or following use of a *cannabis* product.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

The figures together with the following detailed description make apparent to those skilled in the art how the disclosure may be implemented in practice.

DETAILED DESCRIPTION

Various compositions and methods will be described below to provide an example of an embodiment of each claimed subject matter. No embodiment described below limits any claimed subject matter and any claimed subject matter may cover methods, processes, or compositions that differ from those described below. The claimed subject matter is not limited to compositions or methods having all of the features of any one composition, method, or process described below or to features common to multiple or all of the compositions, or methods described below. It is possible that a composition, method or process described below is not an embodiment of any claimed subject matter. Any subject matter disclosed in a composition, method or process described below that is not claimed in this document may be the subject matter of another protective instrument, for example, a continuing patent application, and the applicants, inventors or owners do not intend to abandon, disclaim or dedicate to the public any such subject matter by its disclosure in this document.

All publications, patents, and patent application are herein incorporated by reference in their entirety to the same extent as if each individual publication, patent or patent application was specifically and indicates to be incorporated by reference in its entirety Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Definitions

Figure 1A:
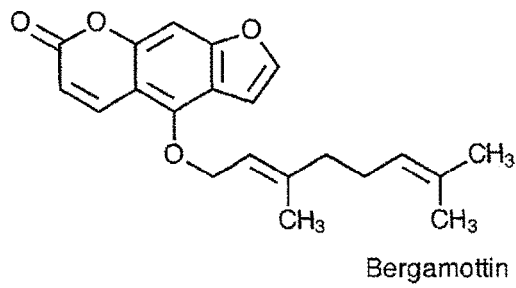
FIGS. 1A-1H provide the chemical structures of certain chemical compounds, notably, bergamottin (FIG. 1A), phloretin (FIG. 1B), piperine (FIG. 1C), ursolic acid (FIG. 1D) cannabidiol (FIG. 1E), apigenin (FIG. 1F), cannabidiolic acid (FIG. 1G) and dihydroxybergamottin (FIG. 1H).
Figure 1B:
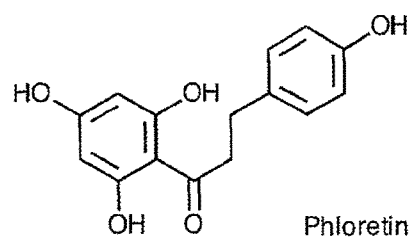
Figure 1C:
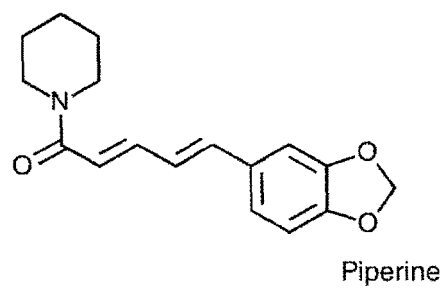
Figure 1D:
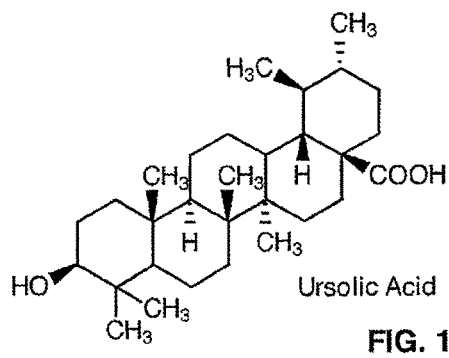
Figure 1E:
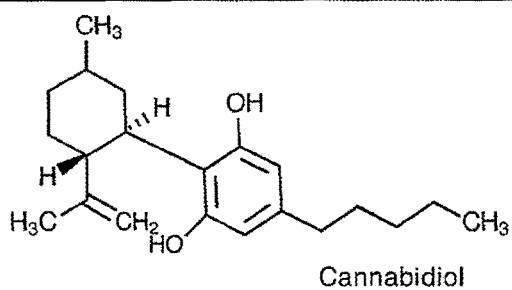
Figure 1F:
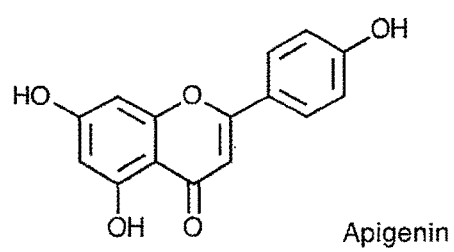

"Apigenin", as used herein, refers to a compound having the chemical structure depicted in FIG. 1F.

Figure 3A:
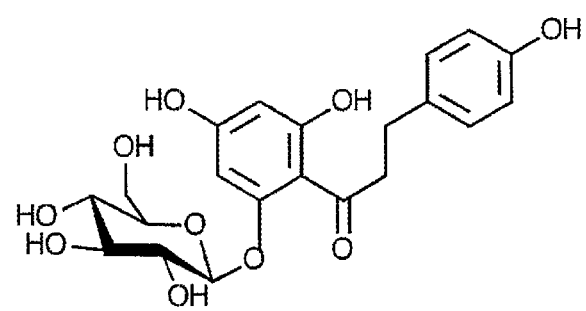
FIGS. 3A & 3B provide exemplary chemical structures of a glycoside of phloretin and apigenin, notably phlorizin (FIG. 3A) and apiin (FIG. 3B).
Figure 3B:
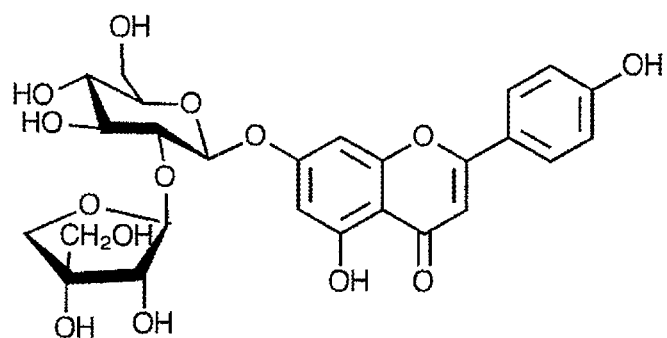

"Apigenin glycoside", as used herein refers to apigenin derivatives wherein apigenin is modified to comprise one or more glycosides, preferably, but not limited to, those made through O-linkage to one of its phenolic moieties. An example of an apigenin glycoside is apiin (FIG. 3B).

"Bergamottin" as used herein refers to a compound having the chemical structure depicted in FIG. 1A.

"Cannabidiol" or "CBD", as may be used interchangeably herein, refers to a compound having the chemical structure depicted in FIG. 1E.

Figure 1G:
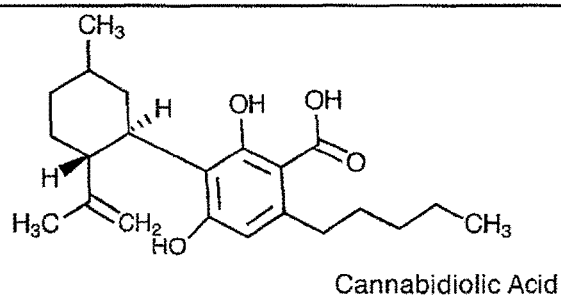

"Cannabidiolic acid", as used herein, refers to a compound having the chemical structure depicted in FIG. 1G.

"Cannabis", as used herein, refers to a preparation comprising one or more cannabinoids obtained or obtainable from a plant belonging to the genus Cannabis, including Cannabis sativa, Cannabis ruderalis and Cannabis indica, including any plant line or cultivar thereof. Cannabis preparations include, without limitation, flower bud preparations, hash, hashish, hash oil, alcohol extracts or tinctures and kief. The concentration of cannabinoids, as well as the purity among different cannabis preparations may vary.

"Cannabinoid" refers to a family of compounds acting on cannabinoid receptors. Cannabinoids usually contain a pyrane ring, preferably a 1,1'-di-methyl-pyrane ring, a variedly derivatized aromatic ring and a variedly unsaturated cyclohexyl ring and their immediate chemical precursors and derivatives, and include, but are not limited to, cannabigerol (CBG); cannabichromene (CBC); cannabidiol (CBD); tetrahydrocannabinol (THC), including without limitation, $\Delta^8$-tetrahydrocannabinol ($\Delta^8$-THC), $\Delta^9$-tetrahydrocannabinol ($\Delta^9$-THC), 11-hydroxy-$\Delta^9$-tetrahydrocannabinol and 11-nor-9-carboxy-$\Delta^9$-tetrahydrocannabinol; cannabinol (CBN); cannabinodiol (CBDL); cannabicyclol (CBL); cannabivarin (CBV); tetrahydrocannabivarin (THCV); cannabidivarin (CBDV); cannabichromevarin (CBCV); cannabigerovarin (CBGV); cannabigerol monomethyl ether (CBGM); cannabinerolic acid and cannabidiolic acid (CBDA); cannabinol propyl variant (CBNV); cannabitriol (CBO); tetrahydrocannabinolic acid (THCA); and tetrahydrocannabivarinic acid (THCVA).

Figure 1H:
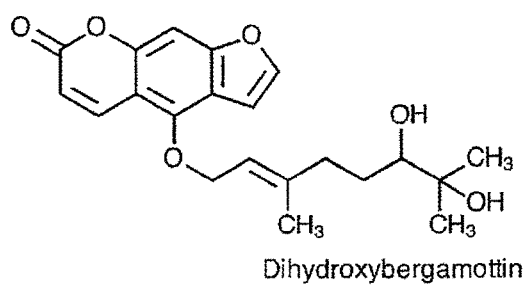
Figure 2A:
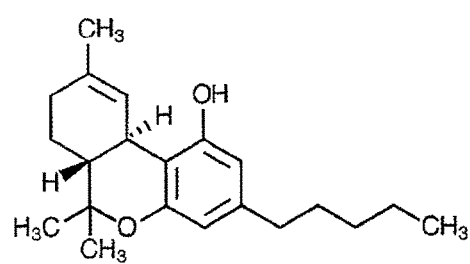
FIGS. 2A-2D provide the chemical structures of certain chemical compounds, notably $\Delta^9$-tetrahydrocannabinol ($\Delta^9$-THC) (FIG. 2A), $\Delta^8$-tetrahydrocannabinol ($\Delta^8$-THC) (FIG. 2B), $\Delta^9$-tetrahydrocannabinol ($\Delta^9$-THC), 11-hydroxy-$\Delta^9$-tetrahydrocannabinol (FIG. 2C) and 11-nor-9-carboxy-$\Delta^9$-tetrahydrocannabinol (FIG. 2D)
Figure 2B:
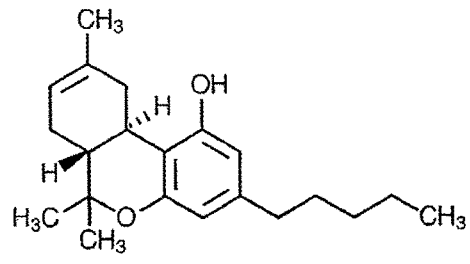
Figure 2C:
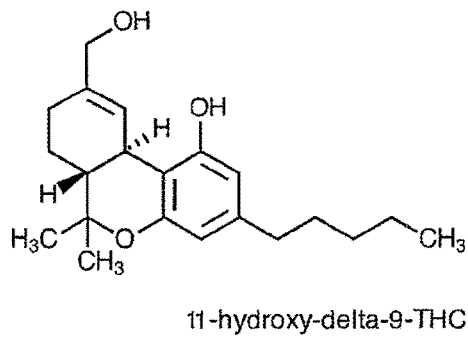
Figure 2D:
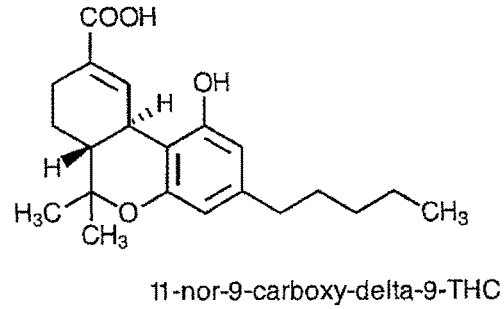

"Dihydroxybergamottin", as used herein, refers to a compound having the chemical structure depicted in FIG. 1H.

"Phloretin", as used herein, refers to a compound having the chemical structure depicted in FIG. 1B.

"Phloretin glycoside", as used herein refers to a phloretin derivatives, wherein phloretin is modified to comprise one or more glycosides, preferably, but not limited to, those made through O-linkage to one of its phenolic moieties. An example of a phloretin glycoside is phlorezin (FIG. 3A).

"Piperine", as used herein refers to a compound having the chemical structure depicted in FIG. 1C.

"Tetrahydrocannabinol" or "THC" refers collectively to $\Delta^9$-tetrahydrocannabinol (which may also be referred to as "$\Delta^9$-THC") and the following derivatives: A-tetrahydrocannabinol (which may also be referred to as "$\Delta^8$-THC"), 11-hydroxy-$\Delta^9$-tetrahydrocannabinol (which may also be referred to as "11-hydroxy-$\Delta^9$-THC"), and 11-nor-9-carboxy-$\Delta^9$-tetrahydrocannabinol (which may also be referred to as "11-nor-9-carboxy-$\Delta^9$-THC"). Each of the foregoing compounds may also be referred to herein individually and, as used herein, shall then be referring to the compounds having the chemical structures depicted in FIGS. 2A-2D.

"Ursolic acid", as used herein, refers to a compound having the chemical structure depicted in FIG. 1D.

It should be noted that terms of degree such as "substantially", "essentially", "about" and "approximately" as used herein mean a reasonable amount of deviation of the modified term such as that the end result is not significantly changed. These terms of degree should be construed as including a deviation of the modified term if this deviation would not negate the meaning of the term it modifies.

It is further noted that, as used in this specification and the appended claims, the singular forms "a", "an" and "the" include plural referents unless the content clearly dictates otherwise.

It is further noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

General Implementation

As hereinbefore mentioned, the present disclosure relates to compositions for the prevention and treatment of anxiolytic conditions associated with the use of cannabis. The herein provided compositions provide a natural treatment option and the active compounds can be obtained in a generally regarded as safe (GRAS) form. Furthermore the active compounds of the present disclosure exhibit a low $IC_{50}$, i.e., the active compounds are efficacious at low concentrations, thus reducing the potential toxic effects associated with use of the compounds. In particular, medicinal compositions combining two or more of the active compounds of the present disclosure are unexpectedly potent. The compositions of the present disclosure contain active compounds that can readily be obtained and the medicinal compositions can be made on an industrial scale.

Accordingly, the present disclosure provides, in at least one embodiment, a medicinal composition for the prevention or treatment of an anxiolytic condition associated with the use of cannabis, the composition comprising cannabinol or cannabidiolic acid, and at least one of the following chemical compounds:
  (a) bergamottin or dihydroxybergamottin;
  (b) phloretin or a phloretin glycoside;
  (c) piperine;
  (d) apigenin or an apigenin glycoside; and
  (e) ursolic acid.

In another embodiment, the present disclosure provides a medicinal composition for the prevention or treatment of an anxiolytic condition associated with the use of cannabis, the composition comprising cannabidiol or cannabidiolic acid and at least two of the following chemical compounds:
  (a) bergamottin or dihydroxybergamottin;
  (b) phloretin or a phloretin glycoside;
  (c) piperine;
  (d) apigenin or an apigenin glycoside; and
  (e) ursolic acid.

In yet another embodiment, the present disclosure further provides, a medicinal composition for the prevention or treatment of an anxiolytic condition associated with the use of cannabis, the composition comprising cannabidiol or cannabidiolic acid and at least three of the following chemical compounds:
  (a) bergamottin or dihydroxybergamottin;
  (b) phloretin or a phloretin glycoside;
  (c) piperine;
  (d) apigenin or an apigenin glycoside; and
  (e) ursolic acid.

In yet another embodiment, the present disclosure further provides a medicinal composition for the prevention or treatment of an anxiolytic condition associated with the use of *cannabis*, the composition comprising cannabidiol or cannabidiolic acid and at least four of the following chemical compounds:

(a) bergamottin or dihydroxybergamottin;
(b) phloretin or a phloretin glycoside;
(c) piperine;
(d) apigenin or an apigenin glycoside; and
(e) ursolic acid.

In yet another embodiment, the present disclosure further provides a medicinal composition for the prevention or treatment of an anxiolytic condition associated with the use of *cannabis*, the composition comprising the following chemical compounds:

(a) bergamottin or dihydroxybergamottin;
(b) phloretin or a phloretin glycoside;
(c) piperine;
(d) apigenin or an apigenin glycoside;
(e) ursolic acid; and
(f) cannabidiol or cannabidiolic acid.

In some embodiments, the compounds are synthesized chemically.

In some embodiments, the compounds are obtained from natural sources, notably plants including a variety of plant parts, such as roots, stems, leaves, flowers, seeds and fruits.

In some embodiments, bergamottin or dihydroxybergamottin is obtained from plants belonging to the genus *Citrus*, including *Citrus* x *paradisi* (grapefruit), notably from the fruit juice of *Citrus* x paradise, including any varieties or cultivars thereof.

In some embodiments, phloretin is obtained from plants belonging to the genus *Malus*, including *Malus domestica* (apple) or from plants belonging to the genus *Prunus*, including *Prunus mandshurica* (Manchurian apricot), notably from the leaves of *Malus domestica* or *Prunus mandshurica*, including any varieties or cultivars thereof.

In some embodiments, piperine is obtained from plants belonging to the genus *Piper*, including *Piper nigrum* (black pepper), *Piper longum* (long pepper), *Piper officinarum* (long pepper) and *Piper guineense* (West-African pepper), notably from the fruits of *Piper nigrum*, *Piper longum*, *Piper officinarum* or *Piper guineense*.

In some embodiments, apigenin is obtained from plants belonging to the genus *Petrosilinum*, including *Petrosilinum crispum* (parsley), plants belonging to the genus *Apium*, including *Apium graveolens* (celery) and *Apium graveolens* var. *rapaceum* (turnip-root), plants belonging to the genus *Matricaria* or *Chamaemelum*, including *Matricaria chamomilla* (chamomile) and *Chamamaemelum nobile* (chamomile), including any varieties or cultivars thereof.

In some embodiments, ursolic acid is obtained from plants belonging to the genus *Mirabilis*, including *Mirabilis Jalapa* (four 'o clock flower), plants belonging to the genus *Malus*, including *Malus domestica* (apple), plants belonging to the genus *Ocimum*, including *Ocimum basilicum* (basil), plants belonging to the genus *Vaccinium*, including *Vaccinium myrtillus* (bilberry) *Vaccinium oxycoccus* (cranberry and *Vaccinum macrocarpon* (cranberry), plants belonging to the genus *Sambucus*, including *Sambucus nigra* (elderberry), plants belonging to the genus *Mentha*, including *Mentha* x *peperita* (peppermint), plants belonging to the genus *Rosmarinus*, including *Rosmarinus officinalis* (rosemary), plants belonging to the genus *Lavandula*, including *Lavandula angustifolia* (lavender), plants belonging to the genus *Oreganum*, including *Origanutn vulgare* (oregano), plants belonging to the genus *Thymus*, including *Thymus vulgaris* (thyme), plants belonging to the genus *Crataegus*, including *Crataegus monogyna* (hawthorn) and plants belonging to the genus *Prunus*, including *Prunus domestica* (European plum), including any varieties or cultivars thereof.

In some embodiments, cannabidiol is obtained from plants belonging to the genus *Cannabis*, including *Cannabis sativa*, *Cannabis ruderalis* and *Cannabis* indica, notably from the flowers of *Cannabis sativa*, *Cannabis ruderalis* and *Cannabis* indica, including any varieties or cultivars thereof.

In some embodiments of the present disclosure, the compounds of the present disclosure are extracted from plants, including any of the hereinbefore mentioned plants or mixtures thereof. Extraction techniques that can be used include extraction from plant parts including roots, stems, leaves, flowers and fruits, wherein the plant parts may be wet or dried, using, for example, a hydrator. Extraction can be carried out using a range of different solvents. Aqueous extracts can be obtained by extraction in water or an aqueous buffer. Organic extracts can be obtained using a range of different organic solvents, for example, methanol, ethanol, hexanol, hexane, phenol, chloroform or ethyl acetate, or mixtures, or sequential use thereof. Mixed mode extraction can also be carried out using microwave assisted extraction of moisture containing plant materials in organic solvents. Extraction can be carried out using gases (such as $CO_2$) liquified under subcritical and supercritical pressure conditions and these liquefied gases can be used with and without co-solvents.

Extraction generally initially involves homogenization of plants or plant parts, using in some embodiments homogenizing equipment, such as a grinder or mill, and thereafter mixing of homogenized plants or plant parts with the selected solvent, and subsequent use of a separation device to obtain one or more fractions comprising plant or plant part constituents. The insoluble fraction may be separated from the soluble fraction. Where solvent mixtures are used, two or more solvent phases may be obtained and the phases may be separated into two or more fractions. Furthermore, filtration devices may be used to prepare one or more plant part fractions. Filtration devices may vary, and may be relatively crude, e.g., a strainer or paper filter (e.g. Whatman paper), or the filtration devices may be more refined, for example, a chromatography medium and column chromatography may be used, e.g., high performance liquid chromatography (HPLC) and can also involve the use of ultrafiltration technologies such as tangential flow hollow fibre filtration. Sequential combinations of various of the aforementioned methodologies may also be used, in each step enriching for a desired compound which can be a liquid, semisolid, or powder. In this manner, each of the compounds of the present disclosure may be extracted from plants, and an extract or composition comprising these compounds in a more or less pure form, substantially pure form, or pure form can be obtained.

Plant extracts may also be purchased from vendors selling plant or herbal extracts. For example, plant extracts comprising apigenin may be purchased from www.buyextracts.com/apigenin; plant extracts comprising piperine may be purchased from www.buyextracts.com/piperine; plant extract comprising phloretin may be purchased from www.alibaba.com/product-detail/Natural-Apple-Tree-Bark-Extract-with 1861604321.html; and plant extracts comprising cannabidiol or cannabidiolic acid may be purchased from https://pluscbdoil.com/cbd-products/cbd-oil-concentrates/pluscbd-total-plant-complex-oral-applicators/or from http://sanahempjuice.com/en/order-now/raw-sana-hemp-juice-powder-90-vcaps.html?cr exp=s&cr cid=132834398.

In some embodiments, the compositions of the present disclosure include less than 99% (w/w), less than 98% (w/w), less than 97% (w/w), less than 96% (w/w), less than 95% (w/w) or less than 90% (w/w) of bergamottin or dihydroxybergamottin.

In some embodiments, the compositions of the present disclosure include less than 99% (w/w), less than 98% (w/w), less than 97% (w/w), less than 96% (w/w), less than 95% (w/w) or less than 90% (w/w) of phloretin.

In some embodiments, the compositions of the present disclosure include less than 99% (w/w), less than 98% (w/w), less than 97% (w/w), less than 96% (w/w), less than 95% (w/w) or less than 90% (w/w) of piperine.

In some embodiments, the compositions of the present disclosure include less than 99% (w/w), less than 98% (w/w), less than 97% (w/w), less than 96% (w/w), less than 95% (w/w) or less than 90% (w/w) of ursolic acid.

In some embodiments, the compositions of the present disclosure include less than 99% (w/w), less than 98% (w/w), less than 97% (w/w), less than 96% (w/w), less than 95% (w/w) or less than 90% (w/w) of cannabidiol or cannabidiolic acid.

In embodiments hereof where mixtures are prepared, the relative quantities
of the desired compounds in the mixture may vary. In some embodiments, equal or approximately equal quantities on a weight basis of two or more compounds are mixed. The obtained compositions, whether comprising two or more of the desired compounds, can be analyzed using a variety of chemical assays and techniques, including, but not limited to, mass spectrometry (MS) techniques, and nuclear magnetic resonance (NMR) techniques, gas chromatography techniques, liquid chromatography techniques and immunoassay techniques.

The obtained compositions, whether comprising one or more of the desired compounds, can further be assayed and evaluated for their potential to modulate a physiological response to *cannabis*. In accordance herewith these assays may be conducted in vivo or in vitro. In some embodiments, the composition comprising cannabidiol is assayed for interaction with cannabinoid receptors. In some embodiments, the composition is assayed for inhibition of the conversion of $\Delta^9$-tetrahydrocannabinol to 11-hydroxy-$\Delta^9$-tetrahydrocannabinol. In some embodiments, the composition is assayed for inhibition of the enzymes cytochrome P450 (CYP450) enzymes, including the enzymes CYP2C and CYP3A4. In some embodiments, a composition comprising bergamottin and/or phloretin is assayed for inhibition of CYP2C or CYP34A.

In some embodiments, human test subjects may be used to evaluate their potential to modulate a physiological response to *cannabis*. Using these assays, the compositions of the present disclosure may be optimized or adjusted, for example, by preparing a plurality of sample compositions, each including a different concentration of one or more compound, assaying each sample, for example, with respect to interaction with a cannabinoid receptor or with respect to inhibition of a CYP450 enzyme, or with respect to an in vivo anti-anxiolytic effect. The, a composition may be selected that comprises a concentration of one or more compounds that provides the most desirable effect.

The compounds of the present disclosure may be formulated for use as a medicinal composition. Thus, the present disclosure further includes medicinal compositions comprising the compounds prepared in accordance with the methods of the present disclosure. The quantity of the desired compounds in a medicinal composition may vary, but typically does not exceed 90%, 80%, 70%, 60%, 50%, 40%, 30%, 20%, 10%, 9%, 8%, 7%, 6%, 5%, 3%, 2% or 1% by weight of the medicinal composition.

Medicinal compositions comprising one or more of the compounds of the present disclosure in some embodiments further comprise auxiliary substances, such as, for example, an excipient, diluent or carrier. These auxiliary substances are generally medicinally acceptable agents that may be administered without undue toxicity. Medicinally acceptable excipients include, but are not limited to, liquids such as water, saline, glycol, polyethyleneglycol, hyaluronic acid, glycerol, ethanol, dimethylsulfoxide, fatty alcohols, triglycerides, partial esters of glycerine, and the like. Medicinally acceptable salts can also be included therein, for example, mineral acid salts such as hydrochlorides, phosphates, sulfates, and the like; and the salts of organic acids such as acetates, propionates, benzoates, and the like. It is also suitable, although not required, that the composition will contain a medicinally acceptable excipient that serves as a stabilizer. Examples of suitable carriers that also act as stabilizers include, without limitation, pharmaceutical grades of dextrose, sucrose, lactose, sorbitol, inositol, dextran, starch, talc, gum Arabic and the like. Other suitable carriers include, again without limitation, starch, cellulose, sodium or calcium phosphates, citric acid, glycine, polyethylene glycols (PEGs), and combinations thereof. Examples of suitable diluents include aqueous diluents such as water or saline, and non-aqueous diluents such as oils, including, for example, MCT oils. Coloring and flavoring agents may also be added in particular in compositions for oral, buccal or sublingual administration.

The medicinal composition may be formulated for oral, buccal, sublingual, pulmonary, topical, transdermal, nasal or intravenous administration and other routes of administration as desired. The medicinal compositions may be self-administered or administered by a health professional. Other dosage forms include capsules, including gel capsules; tablets; pills; powders; orally dissolving strips or tablets, aerosols and suppositories.

Suitable dosages of the medicinal compositions for use in the methods of the present disclosure will depend upon a number of factors including, for example, age and weight of an subject being treated, severity of a anxiolytic condition, specific compounds included in the composition to be used, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until sufficient to prevent or ameliorate anxiolytic conditions experienced by a user of *cannabis*. Alternatively, one skilled in the art can begin with a high dosage that can be decreased until reaching a minimum dosage needed to prevent or ameliorate anxiolytic conditions experienced by a user of *cannabis*.

In one embodiment, the medicinal compositions of the present disclosure further include an antioxidant as an auxiliary substance. Antioxidants that may be used in accordance with the present disclosure include ellagitannins and hydrolysis products of ellagitannnis, such as ellagic acid, gallotannins and hydrolysis products of gallotannins, epigallocatchin gallate, gossypetin and gossypetin glycosides, naringenin and naringenin glycosides, myricetin and myricetin glycosides, quercetin and quercetin glycosides, and kaempferol and kaempferol glycosides. Further antioxidants that may be used are fruit extracts, for example berry extracts, including for example raspberry extracts. Antioxidants used herein may be obtained from a natural source or synthetically prepared.

In one embodiment, the medicinal compositions of the present disclosure may further include an anxiolytic active compound, other than:
 (a) bergamottin or dihydroxybergamottin;
 (b) phloretin or a phloretin glycoside;
 (c) piperine;
 (d) apigenin or an apigenin glycoside;
 (e) ursolic acid; and
 (f) cannabidiol or cannabidiolic acid;
but including, without limitation, a synthetic anxiolytic compound such as: a barbiturate; a benzodiazepine, for example, alprazolam, bromazepam, chlordiazepoxide, clonazepam, chlorazepate, diazepam, flurazepam, lorazepam, oxazepam, tempazepam, triazolam and tofizapam; a carmabate; an opiate, or an antidepressant; or a natural anxiolytic compound such as plant material and/or extracts and/or purified constituents from Valeriana spp.; or such as an essential oil or essential oil constituent such as, for example, myrcene, linalool, limonene, caryophyllen, turpinolene, pinene.

In accordance herewith the medicinal compositions of the present disclosure may be used to treat or prevent anxiolytic conditions associated with cannabis use in a subject in need thereof. As used herein, a "subject in need" refers to an individual at risk for or having anxiety associated with cannabis use. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of subjects "in need" of assistance in addressing one or more specific conditions noted herein), not all individuals will fall within the subset or subclass of individuals as described herein. In particular, the subject in need is a human. The subject in need can also be, for example, a research animal such as, for example, a non-human primate, a mouse, a rat, a rabbit, a cow, a pig, and other types of research animals known to those skilled in the art.

The medicinal composition may be administered prophylactically, i.e., prior to use of cannabis, for example about 2 hours, 1 hour, 30 minutes, 15 minutes or 5 minutes before cannabis use, or following use of cannabis. Cannabis use includes any form of cannabis use by a person, including use via any administration route, including, without limitation, pulmonary, oral, buccal or sublingual administration, or via any administration means including in the form of an inhaled or smoked substance, or in edible form, for example in the form of cake, cookies, chocolate, popcorn, beer etc. Cannabis use further includes the use of any cannabinoid containing substance, including, without limitation, any THC containing substance, and further including, without limitation, any containing $\Delta^9$-tetrahydrocannabinol substance, including without limitation, flowerbuds, hash, hasish, kief, and hash oil obtained from Cannabis sativa plants. Cannabis use further includes medical cannabis use and recreational cannabis use, and medicinal compositions of the present disclosure may be administered to cannabis-naïve individuals or to individuals who have a prior cannabis use experience. Cannabis use further includes self-administration of cannabis or administration by a medical professional, including the act of prescribing the use of cannabis. Thus a physician prescribing the self-administration of cannabis to a patient is deemed to be administering cannabis.

In accordance herewith a range of anxiolytic conditions associated with the use of cannabis may be prevented or treated including, without limitation, generalized or inconcrete anxiety, acute uncontrolled anxiety, panic disorder, phobia, for example, claustrophobia, agoraphobia, social phobia or any other phobia, including, but not limited to, fear of particular objects, subjects, animals or situations, in the form of phobia of height, of medical procedures, open or closed spaces, etc., an obsessional condition or an obsessive-compulsive disorder, post-traumatic stress disorder and acute stress disorder.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1: Formulation for the Treatment of Cannabis Induced Anxiety

| Compound | Amount in Composition (mg) |
| --- | --- |
| Dried hemp aerials powder | 500 |
| Apple peel extract powder | 100 |
| Parsley extract powder | 100 |
| Black pepper extract powder | 50 |
| Raspberry extract powder | 100 (obtainable from www.berrihealth.com/collections/all/products/freeze-dried-black-raspberry-powder) |

Example 2: Formulation for the Treatment of Cannabis Induced Anxiety

| Compound | Amount in Composition (mg) |
| --- | --- |
| CDB/CBDA | 25 |
| Phloretin | 5 |
| Apigenin | 5 |
| Piperine | 5 |
| Ellagic Acid | 20 (obtainable from www.buyextracts.com/ellagic-acid) |

What is claimed is:

1. A method for treating post traumatic stress disorder in a human in need thereof who is being administered cannabis consisting essentially of administering to the human in need thereof pure cannabidiol and a compound selected from the group consisting of bergamottin, dihydroxybergamottin, phloretin, a phloretin glycoside, piperine, apigenin, an apigenin glycoside, ursolic acid and combinations thereof,
  wherein the pure cannabidiol and the compound is administered prior to or following use of the cannabis by the human in need thereof.

* * * * *